United States Patent
Karam et al.

(10) Patent No.: US 8,890,073 B2
(45) Date of Patent: Nov. 18, 2014

(54) SYSTEMS AND METHODS FOR DETECTING AND/OR IDENTIFYING MATERIALS BASED ON ELECTROMAGNETIC RADIATION

(75) Inventors: Mostafa A. Karam, Moorpark, CA (US); A. Douglas Meyer, Woodland Hills, CA (US); Charles H. Volk, Newbury Park, CA (US); Azmat H. Siddiqi, Belmont Shore, CA (US)

(73) Assignee: Northrop Grumman Guidance and Electronics Company, Inc., Woodland Hills, CA (US)

( * ) Notice: Subject to any disclaimer, the term of this patent is extended or adjusted under 35 U.S.C. 154(b) by 223 days.

(21) Appl. No.: 13/432,606

(22) Filed: Mar. 28, 2012

(65) Prior Publication Data

US 2012/0248314 A1 Oct. 4, 2012

Related U.S. Application Data

(60) Provisional application No. 61/468,424, filed on Mar. 28, 2011, provisional application No. 61/476,542, filed on Apr. 18, 2011.

(51) Int. Cl.
G01J 5/10 (2006.01)
G01S 13/88 (2006.01)
G01N 21/35 (2014.01)
G01K 11/00 (2006.01)

(52) U.S. Cl.
CPC ........... *G01S 13/887* (2013.01); *G01N 21/3563* (2013.01); *G01K 11/006* (2013.01); *G01N 21/3581* (2013.01); *G01J 5/10* (2013.01)
USPC ..................................................... 250/341.3

(58) Field of Classification Search
USPC ................. 250/341.3, 341.8, 338.1
See application file for complete search history.

(56) References Cited

U.S. PATENT DOCUMENTS 3,748,484 A * 7/1973 Covault ........................ 250/225
4,875,175 A 10/1989 Egee et al.
(Continued)

FOREIGN PATENT DOCUMENTS

EP 0 967 459 A1 12/1999
WO WO 99/28715 6/1999

OTHER PUBLICATIONS

Co-Pending Application Entitled: "*Systems and Method for Detecting and/or Identifying Materials*".

*Primary Examiner* — David Porta
*Assistant Examiner* — Faye Boosalis
(74) *Attorney, Agent, or Firm* — Tarolli, Sundheim, Covell & Tummino LLP

(57) ABSTRACT

One embodiment of the invention includes a material detection and/or identification system. The system includes an electromagnetic (EM) sensor system configured to collect EM radiation from a region of interest. The collected EM radiation could comprise orthogonally-polarized EM radiation. The system also includes a processing unit configured to detect and identify a material of interest in the region of interest. As an example, the processing unit could measure reflectivity data associated with a material of interest based on the collected EM radiation and calculate a refractive index of a material of interest based on the measured reflectivity data, such that the material of interest is identified based on the refractive index. The processing unit can also be configured to calculate a surface roughness associated with the material, such that the refractive index can be calculated based on the surface roughness associated with the material.

20 Claims, 5 Drawing Sheets

(56) References Cited

U.S. PATENT DOCUMENTS

| | | |
|---|---|---|
| 5,652,597 A | 7/1997 | Caille |
| 5,757,496 A | 5/1998 | Yamazaki |
| 6,545,763 B1 | 4/2003 | Kim et al. |
| 6,777,684 B1 | 8/2004 | Volkov et al. |
| 6,850,543 B2 | 2/2005 | Cundiff et al. |
| 7,280,078 B2 | 10/2007 | Salsman et al. |
| 7,306,367 B2 | 12/2007 | Salem et al. |
| 7,339,682 B2 | 3/2008 | Aiyer et al. |
| 7,471,392 B2 | 12/2008 | Norton et al. |
| 7,489,391 B2 | 2/2009 | Engheta et al. |
| 7,515,347 B2 | 4/2009 | Hauschild et al. |
| 7,616,323 B2 | 11/2009 | De Lega et al. |
| 7,687,773 B2 | 3/2010 | Siegel et al. |
| 2003/0163042 A1 | 8/2003 | Salmon |
| 2004/0136041 A1 | 7/2004 | Togino |
| 2007/0014319 A1 | 1/2007 | Hill et al. |
| 2008/0074674 A1 | 3/2008 | Chen et al. |
| 2008/0306719 A1 | 12/2008 | Freier |
| 2009/0268205 A1* | 10/2009 | Naya .............................. 356/445 |
| 2010/0007863 A1 | 1/2010 | Jordanoska |
| 2010/0025599 A1* | 2/2010 | Bowers et al. ............. 250/503.1 |
| 2011/0004091 A1 | 1/2011 | Brooks et al. |

* cited by examiner

SYSTEMS AND METHODS FOR DETECTING AND/OR IDENTIFYING MATERIALS BASED ON ELECTROMAGNETIC RADIATION

RELATED APPLICATIONS

The present invention claims priority from U.S. Provisional Application Ser. No. 61/468,424, filed 28 Mar. 2011 and U.S. Provisional Application Ser. No. 61/476,542, filed 18 Apr. 2011, both of which are herein incorporated by reference in their entirety.

TECHNICAL FIELD

The present invention relates generally to electromagnetic sensor systems, and specifically to systems and methods for detecting and/or identifying materials based on electromagnetic radiation.

BACKGROUND

There has been an ever increasing demand in security, warfare, and peacekeeping applications for a manner to accurately detect the presence of dangerous materials, such as concealed weapons, chemicals, or explosives. In the case of concealed explosives or chemicals, it is typically necessary to detect the materials from a suitable standoff distance, so as to avoid danger to the individuals that attempt to detect the concealed materials. Furthermore, it may be desirable to identify the specific type of materials, such as to determine a source of the dangerous materials or to assess the potential for damage or harm resulting from detonation or release of the dangerous materials.

There are many techniques that have been efficiently used in detecting whether certain dielectric materials, such as chemicals or explosives, are present and/or in identifying the type of dielectric material. For example, typical detection/identification systems include cavity resonators, spectroscopes, time domain reflectors, and a variety of other techniques. However, most such techniques are either laboratory based techniques or contact techniques. As a result, the techniques are unable to be used in the context of a field operation or at a large public event (LPE) where farther standoff distances are required. In addition, certain detection techniques are unable to penetrate intervening materials, such as clothing and/or precipitation or atmospheric conditions. Furthermore, the efficiency of detecting the dielectric materials and/or classifying the dielectric materials as being specific dangerous materials can be degraded by irregularities of the surface of the materials.

SUMMARY

One embodiment of the invention includes a material detection system. The system includes an EM sensor system configured to collect EM radiation from a region of interest. The system also includes a processing unit configured to measure reflectivity data associated with a material of interest in the region of interest based on the collected EM radiation and to calculate a refractive index of a material of interest based on the measured reflectivity data. The processing unit can further be configured to identify the material of interest based on the refractive index of the material of interest.

Another embodiment of the invention includes a method for detecting and identifying a material in a region of interest. The method includes collecting orthogonally-polarized EM radiation from a region of interest at an observation angle. The method also includes implementing an algorithm to obtain at least one refractive index value associated with the dielectric material in the region of interest based on wave characteristics associated with the collected orthogonally-polarized EM radiation. The method further includes identifying the dielectric material based on the at least one refractive index value.

Another embodiment of the invention includes a method for determining a refractive index of a material. The method includes collecting orthogonally-polarized EM radiation from the material at an approximately 45 degree observation angle. The method also includes estimating a surface roughness associated with the material based on wave characteristics associated with the collected orthogonally-polarized EM radiation. The method further includes calculating a refractive index of the material based on the surface roughness of the material and based on the wave characteristics associated with the collected orthogonally-polarized EM radiation.

DETAILED DESCRIPTION

The present invention relates generally to electromagnetic sensor systems, and specifically to systems and methods for detecting and/or identifying materials based on electromagnetic (EM) radiation. A detection system can include an EM sensor system and a processing unit. The EM sensor system can be configured to collect radiation from a region of interest. The radiation can include one or more types of radiation, such as millimeter-wave (MMW), terahertz (THz), and/or infrared (IR) radiation from the region of interest. The EM sensor system can be configured as a passive radiometer, or can be configured as an active sensor, such as a backscattering or a bi-static scatterometer/radar. Thus, the EM sensor system can be configured to gather wave-characteristic information regarding the region of interest. As an example, the EM sensor system can be configured to collect radiation of the region of interest, such as orthogonally-polarized radiation, to obtain signal characteristics of the region of interest, such as to detect the presence of an anomaly that can correspond to a dangerous dielectric material.

The processing unit can be configured to implement one or more signal processing algorithms that can detect the presence of the dangerous dielectric material in the region of interest and/or to identify the specific type of dangerous dielectric material. As an example, the processing unit can be configured to calculate the reflectivity of one or more materials in the region of interest. The processing unit can also be configured to calculate refractive index data associated with the detected dielectric materials, such that the refractive index data can be compared with entries in a database to determine the specific type of dielectric materials. As another example, the reflectivity data that can be acquired based on the collected radiation can correspond to horizontal and vertical reflectivities. The horizontal and vertical reflectivities can be implemented to estimate a surface roughness of the material, which can then be implemented to calculate refractive index data associated with the material.

Figure 1:
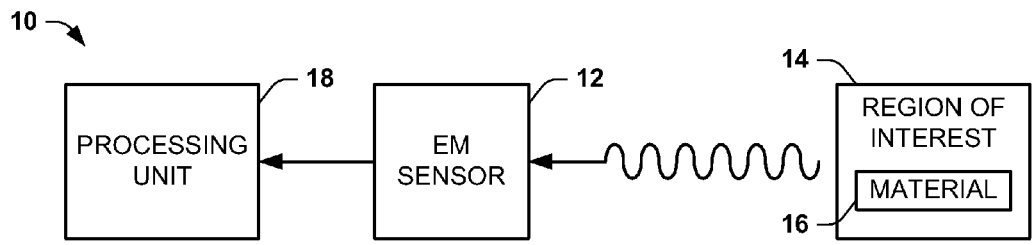
FIG. 1 illustrates an example of a material detection system in accordance with an aspect of the invention.

FIG. 1 illustrates an example of a material detection system 10 in accordance with an aspect of the invention. The material detection system 10 can be implemented in a variety of applications to detect and/or to identify potentially dangerous dielectric materials, such as explosives and/or chemicals. For example, the material detection system 10 can be implemented to scan people in a crowd in a non-invasive manner to detect the presence of concealed weapons, explosives, or improvised explosive devices (IEDs), to scan a large public venue for explosive devices, and/or to scan a region of interest for buried explosives and/or road-side bombs. Thus, the material detection system 10 can be implemented in a variety of applications.

The material detection system 10 includes an EM sensor 12 that is configured to collect radiation from a region of interest 14. The EM sensor 12 can be configured to collect the radiation in any of a variety of frequency bands in the EM frequency spectrum, such as including one or more of millimeter-wave (MMW), terahertz (THz), and infrared (IR) radiation. The EM sensor 12 can be configured as a passive radiometer, or can be an active sensor, such as a scatterometer (e.g., a backscattering or bi-static scatterometer/radar). The EM sensor 12 can thus acquire wave characteristics to detect the presence of a material 16. As an example, the material 16 can be a dangerous material, such as an explosive or hazardous chemical, or can be a weapon. Thus, the region of interest 14 can correspond to a crowd of people, a large public venue, or a geographical area in which the material 16 is concealed or is otherwise obscured from close proximal view.

The EM sensor 12 provides input in the form of wave characteristic data to a processing unit 18. The processing unit 18 can thus be configured to process the wave characteristic data to implement detection and/or possible identification of the material 16. For example, the processing unit 18 can be configured to implement an algorithm based on emissivity, temperature, or a variety of other received wave characteristics of the region of interest 14 to detect an anomaly that could correspond to the presence of the material 16. The processing unit 18 could then implement the algorithm to confirm the presence of the material 16, or could further process the anomaly to determine the specific identity of the material 16. For example, the processing unit 18 could be configured to calculate a refractive index of the material 16, such as based on reflectivity data and an observation angle of the EM sensor 12 relative to the region of interest 14. The processing unit 18 could thus identify the specific material 16 based on the calculated refractive index.

Figure 2:
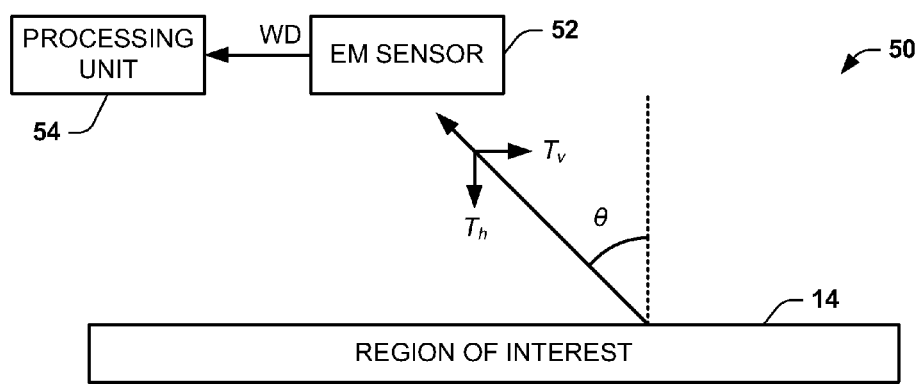
FIG. 2 illustrates yet another example of a material detection system in accordance with an aspect of the invention.

As an example, the material detection system 10 in the example of FIG. 1 can be configured to determine the presence of and identity of the material 16 based on extracting complex refractive index components of the material 16 in terms of orthogonally-polarized reflectivity data and an observation angle. FIG. 2 illustrates an example of a material detection system 50 accordance with an aspect of the invention. The material detection system 50 includes an EM sensor 52 that can correspond to the EM sensor 12 in the example of FIG. 1. Therefore, reference is to be made to the example of FIG. 1 in the following description of the example of FIG. 2. As an example, the EM sensor 52 and a corresponding processing unit can be incorporated into a common field apparatus, such as can be hand-held or otherwise portable.

In the example of FIG. 2, the EM sensor 52 is demonstrated as collecting radiation from a surface of the material 16 at an incidence angle θ. As a first example, the EM sensor 52 can be configured as a dual polarized radiometer that acquires thermal radiations emitted from the surface of the material in the form of two polarized brightness temperatures: a vertical brightness temperature $T_v$ and a horizontal brightness temperature $T_h$. The vertical brightness temperature $T_v$ and the horizontal brightness temperature $T_h$ can be expressed as follows:

$$T_v = (1-R_v)T + R_v T_{sky}$$

$$T_h = (1-R_h)T + R_h T_{sky} \qquad \text{Equations 1}$$

Where:
T is the physical temperature of the material 16;
$T_{sky}$ is the sky brightness temperature;
$R_h$ is the horizontal reflectivity of the material 16; and
$R_v$ is the vertical reflectivity of the material 16.

In Equations 1, the physical temperature T can be measured via a thermal IR radiometer, such as can be included in the EM sensor 52. For example, the thermal IR radiometer could be configured to measure the physical temperature T in a manner substantially similar to as described in Applicant's co-pending application Ser. No. 13.432,558, entitled: "Systems and Methods for Detecting and/or Identifying Materials", filed simultaneously herewith, incorporated herein by reference in its entirety. The sky brightness temperature $T_{sky}$ can be measured by directing the EM sensor 52 toward the sky, similar to as described above in the example of FIG. 4. The calculations of the vertical brightness temperature $T_v$ and the horizontal brightness temperature $T_h$ can be valid at a variety of lower frequencies (e.g., RF, microwave, millimeter wave). At substantially higher frequencies (e.g., terahertz, IR, optics), the vertical brightness temperature $T_v$ and the horizontal brightness temperature $T_h$ and the physical temperature T could be replaced by a corresponding radiance. In the example of FIG. 2, the EM sensor 52 can be configured to provide data associated with the vertical brightness temperature $T_v$, the horizontal brightness temperature $T_h$, and the sky brightness temperature $T_{sky}$ as a signal WD to a processing unit 54, such as can correspond to the processing unit 18 in the example of FIG. 1.

It is to be understood that the dual polarization of the EM sensor 52 could be realized through either the use of two radiometers or a single radiometer. In case of the two radiometers, each radiometer could have a polarization orthogonal to the polarization of the other radiometer. In case of the single radiometer, the two orthogonal polarizations could be achieved through rotating the radiometer around the boresight (i.e., the direction of main beam) of its antenna.

Figure 3:
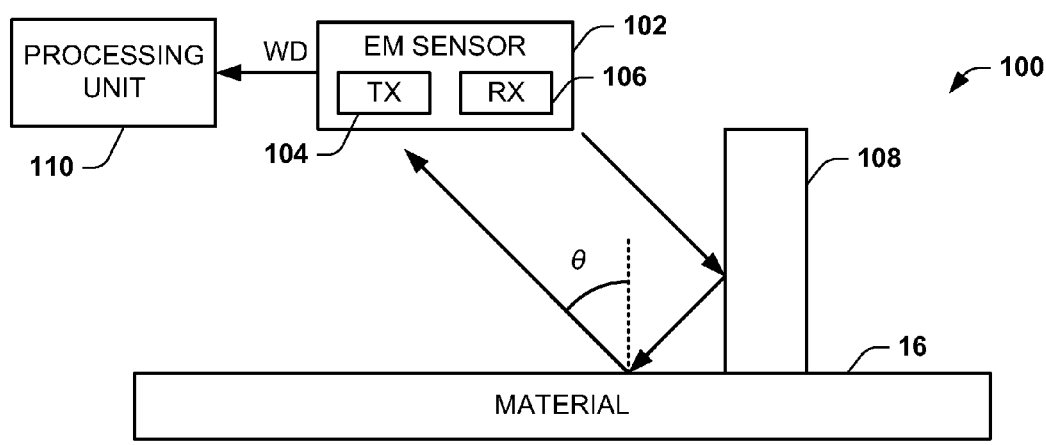
FIG. 3 illustrates yet a further example of a material detection system in accordance with an aspect of the invention.

In the example of FIG. 2, the EM sensor 52 is configured as a passive sensor. However, an active sensor, such as a backscattering or bi-static scatterometer/radar, could instead be implemented for detection of the material 16. FIG. 3 illustrates another example of a material detection system 100 in accordance with an aspect of the invention. The material detection system 100 includes a sensor 102 that can correspond to the EM sensor 12 in the example of FIG. 1. Therefore, reference is to be made to the example of FIG. 1 in the following description of the example of FIG. 3.

In the example of FIG. 3, the sensor 102 can correspond to a backscattering scatterometer/radar. Specifically, in the example of FIG. 3, the sensor 102 includes a transmitter 104 and a receiver 106. The transmitter 104 can be configured to transmit a dual polarized electromagnetic field and the receiver 106 is configured to receive reflected radiation in a backscattering direction. In addition, it is to be understood that the transmitter 104 and the receiver 106 are not limited to being configured as separate sensor elements, but could instead be incorporated in a common sensor element.

The operation of the sensor 102 as a backscattering scatterometer/radar is based on double-bounce signals stemming from the surface of the material 16 and a vertical structure 108. As an example, the backscattering scatterometer implementation for the sensor 102 can be best suited for urban areas where curbs and building walls could act as a vertical structure in creating the double bounce reflected signals for collecting the radiation. The transmitter 104 of the sensor 102 can be used to illuminate the vertical structure 108 with dual polarized EM fields. When the polarized EM fields reach the vertical structure 108, they are reflected toward the surface of the material 16 where they undergo another reflection toward the sensor 102. After accounting for the gain of the antenna(s) of the transmitter 104 and receiver 106 and for other calibration factors, the data received by the receiver 106 for a polarization p (p=v, h) could be expressed as:

$$\mathcal{R}_p = R_{ep} R_{sp} \quad \text{Equation 2}$$

Where:

$R_{ep}$ is the p (p=v, h) polarized reflectivity of the material 16; and $R_{sp}$ is the reflectivity of the vertical structure.

If the reflectivity $R_{sp}$ of the vertical structure 108 is known it could be implemented in Equation 2 to obtain the reflectivity of the material 16. The dual polarization of the sensor 102 could be achieved following similar approaches to that used in example of the sensor 102 being configured as a dual polarized radiometer, such as described above in the example of FIG. 2. Therefore, the sensor 102 can be configured to provide data associated with the vertical brightness temperature $T_v$, the horizontal brightness temperature $T_h$, and the sky brightness temperature $T_{sky}$ as a signal WD to a processing unit 110 in a manner that is substantially similar to the EM sensor 52 in the example of FIG. 2.

While the example of FIG. 3 demonstrates that the sensor 102 is configured as a backscattering scatterometer/radar, it is to be understood that the sensor 102 could instead be configured as a bi-static scatterometer, such that the transmitter 104 and the receiver 106 could be located at separate locations. As an example, the transmitter 104 could be configured to transmit the dual-polarized electromagnetic signals to the material 16, which could then reflect from the surface of the material 16 to be received by the receiver 106 at the separate location. As an example, the configuration of the sensor 102 as a bi-static scatterometer/radar can be well suited for implementation at a large public event (LPE) where the separate locations of the transmitter 104 and the receiver 106 can be specified.

Figure 4:
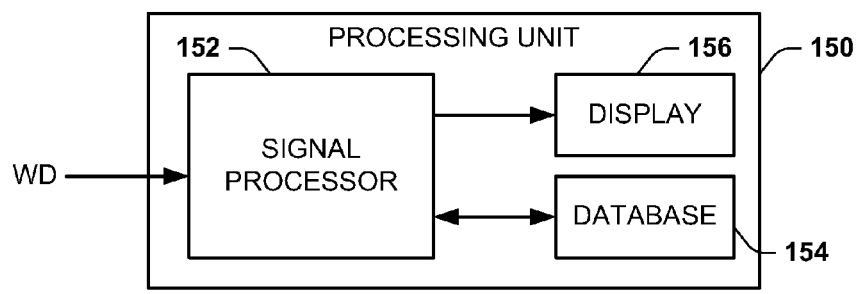
FIG. 4 illustrates another example of a processing unit in accordance with an aspect of the invention.

FIG. 4 illustrates another example of a processing unit 150 in accordance with an aspect of the invention. The processing unit 150 can correspond to the processing unit 54 in the example of FIG. 2 or the processing unit 110 in the example of FIG. 3. Therefore, reference is to be made to the examples of FIGS. 1-3 in the following description of the example of FIG. 4.

The processing unit 150 includes a signal processor 152, a database 154, and a display 156. The signal processor 152 receives the signal WD corresponding to the wave characteristics of the EM radiation collected by the EM sensor 52, such as including the vertical brightness temperature $T_v$, the horizontal brightness temperature $T_h$, and the sky brightness temperature $T_{sky}$. As an example, upon obtaining the vertical brightness temperature $T_v$, the horizontal brightness temperature $T_h$, and the sky brightness temperature $T_{sky}$, as well as the physical temperature T of the region of interest 14, the signal processor 152 can be configured to calculate the vertical and horizontal reflectivities $R_h$, $R_v$ as follows:

$$R_v = \frac{T - T_v}{T - T_{sky}} \quad \text{Equations 3}$$

$$R_h = \frac{T - T_h}{T - T_{sky}}$$

The signal processor 152, upon calculating the vertical and horizontal reflectivities $R_h$, $R_v$, can be configured to calculate refractive index values associated with the material 16. To do so, the signal processor 152 calculates variables P and Q from polarized emissivity values associated with the material 16, as follows:

$$Q = \frac{1 - R_h}{1 + R_h} \quad \text{Equations 4}$$

$$P = \frac{R_h - R_v}{R_h + R_v}$$

The signal processor 152 can then incorporate the observation angle θ to obtain the real part β and imaginary part α of a normal propagation vector ratio of wave propagation vectors associated with the material 16, as follows:

$$Q - 2\beta + Q\beta^2 = -Q\alpha^2 \quad \text{Equations 5}$$

$$\beta = \frac{PQ(\cos^2\theta - \sin^2\theta)}{2\cos^2\theta\{P\cos^2\theta - Q\sin^2\theta\}}$$

$$\alpha = \sqrt{\frac{2\beta}{Q} - (1 + \beta^2)}$$

The signal processor 152 can then implement the real and imaginary parts β, α of the normal propagation vector ratio of wave propagation vectors associated with the material 16 to calculate the determine real ∈' and imaginary ∈'' parts of the relative dielectric constant ∈ in the following manner:

$$\in' = (\beta^2 - \alpha^2)\cos^2\theta + \sin^2\theta$$

$$\in'' = 2\beta\alpha \cos^2\theta \quad \text{Equations 6}$$

Finally, the signal processor 152 can implement the real ∈' and imaginary ∈'' parts of the relative dielectric constant ∈ to calculate the real and imaginary parts of the refractive index of the material 16 in the following manner:

$$\varepsilon_r = \varepsilon'_r - j\varepsilon''_r \quad \text{Equations 7}$$

$$N = \sqrt{\varepsilon_r} = n - j\kappa$$

$$n = \sqrt{0.5\left(\sqrt{\varepsilon'^2 + \varepsilon''^2} + \varepsilon'\right)}$$

$$\kappa = \sqrt{0.5\left(\sqrt{\varepsilon'^2 + \varepsilon''^2} - \varepsilon'\right)}$$

After extracting the refractive index N and associated components n, κ of the material 16 based on Equations 7, the signal processor 152 can identify the specific material corresponding to the material 16. This can be achieved through comparing the refractive index N against known values of refractive indices of explosives or other materials stored in the database 154. If the refractive index N matches a value within the database 154, the signal processor 152 can implement the display 156 to provide the name of the explosive material 16 associated with that value to a user. Otherwise the display 156 can indicate that the material corresponding to the material 16 is unknown.

Accordingly, the examples of FIGS. 2-4 demonstrate another manner in which a potentially dangerous material, such as an explosive, can be detected and/or identified. Specifically, the sensors 52 and 102 can be implemented to receive orthogonally polarized radiation which can be indicative of the refractive index of the material, such that the material can be identified as potentially being an explosive based on the refractive index. As a result, the material detection systems 50 and 100 can be used in a variety of security, military, and/or peacekeeping applications for detecting explosives from sufficiently safe standoff distances.

Referring back to the example of FIG. 1, many of the techniques described herein rely on the reflectivity of the material 16 for detection of and possibly the identification of the material 16. However, the surface of the material 16 may be such that the reflectivity of the material 16 may not be accurate. For example, in MMW frequencies, identifying explosive types within an improvised explosive device (IED) can be based on extracting the refractive index of the explosive, then comparing values of extracted refractive index to a database of refractive indices of known explosives, such as described in Applicant's co-pending application Ser. No. 13/432,558, entitled: "Systems and Methods for Detecting and/or Identifying Materials", filed simultaneously herewith. However, the efficiency of extracting the refractive index may be degraded by the irregularities (i.e., roughness) of the IED surface. Therefore, the processing unit 18 can be configured to estimate a surface roughness of the material 16 and to use the estimate of surface roughness of the material 16 to correct the reflectivity of the material 16.

Figure 5:
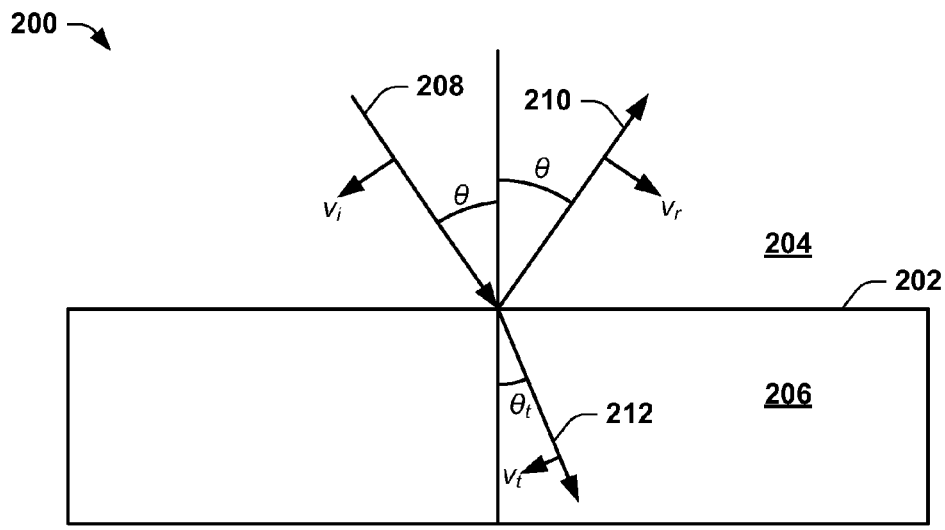
FIG. 5 illustrates another example diagram of propagation vectors in accordance with an aspect of the invention.

FIG. 5 illustrates another example diagram 200 of propagation vectors in accordance with an aspect of the invention. The diagram 200 includes a planar interface 202 separating an upper half space filled with free space 204 and a lower half space occupied by a material 206 having a complex relative dielectric constant $\varepsilon_r$ ($\varepsilon_r = \varepsilon_r' - j\varepsilon_r''$). As an example, the material 206 could be an explosive material. The interface 202 is illuminated by a monochromatic plane wave 208 at an incidence angle θ from the free space 204. A portion 210 of the wave 208 is reflected into the free space 204 and another portion 212 is refracted into the material 206. The horizontal and vertical Fresnel reflection coefficients $r_h(\theta)$, $r_v(\theta)$ characterizing the reflected portion 210 of the wave could be written as follows:

$$r_h(\theta) = \frac{\cos\theta - \cos\theta_t}{\cos\theta + \cos\theta_t} \quad \text{Equations 8}$$

$$r_v(\theta) = r_h(\theta)\left(\frac{\hat{v}_r \cdot \hat{v}_t}{\hat{v}_i \cdot \hat{v}_t}\right)$$

Where:
$\theta_t$ is the refracted angle; and
$\hat{v}_i$, $\hat{v}_r$, and $\hat{v}_t$ are the vertical polarization vectors for the incident, reflected, and refracted waves respectively.

The refracted angle $\theta_t$ is related to the incident angle θ through Snell's law of refraction:

$$\sin\theta = \sqrt{\varepsilon_r}\sin\theta_t \quad \text{Equation 9}$$

Without loss of generality, the azimuth angle φ can be equated to zero, thus leading to the following representation for the vertical polarized vectors $\hat{v}_i$, $\hat{v}_r$, and $\hat{v}_t$:

$$\hat{v}_i = -\cos\theta\hat{x} - \sin\theta\hat{z} \quad \text{Equations 10}$$

$$\hat{v}_r = \cos\theta\hat{x} - \sin\theta\hat{z}$$

$$\hat{v}_t = \frac{1}{\sqrt{\varepsilon_\varepsilon}}(\cos\theta_t\hat{x} - \sin\theta\hat{z})$$

From Equations 10, explicit expressions for the vector product quantities of Equations 8 could be rewritten as:

$$(\hat{v}_r \cdot \hat{v}_t) = \frac{1}{\sqrt{\varepsilon_r}}(\cos\theta\cos\theta_t + \sin^2\theta) \quad \text{Equations 11}$$

$$(\hat{v}_i \cdot \hat{v}_t) = \frac{1}{\sqrt{\varepsilon_r}}(-\cos\theta\cos\theta_t + \sin^2\theta)$$

Now introducing Equations 11 into Equations 8 can provide an explicit expression for the vertically polarized reflection coefficient, as follows:

$$r_v(\theta) = r_h(\theta)\left(\frac{\sin^2\theta - \cos\theta\cos\theta_t}{\sin^2\theta + \cos\theta\cos\theta_t}\right) \quad \text{Equation 12}$$

A material measurement device, such as could be implemented in the processing unit 18 in the example of FIG. 1, can implement a relationship between Fresnel reflection coefficients $r_h(\theta)$, $r_v(\theta)$ to estimate the surface roughness of the material 202. Specifically, using Snell's law, as provided in Equation 9, the cosine of the refractive angle can be expressed as:

$$\cos\theta_t = \sqrt{\varepsilon_r - \sin^2\theta} = \beta - j\alpha \quad \text{Equation 13}$$

Equation 13 can be introduced into Equations 8 and Equation 12 to provide:

$$r_h(\theta) = \frac{\cos\theta - \beta + j\alpha}{\cos\theta + \beta - j\alpha} \quad \text{Equations 14}$$

$$r_v(\theta) = r_h(\theta)\left(\frac{\sin^2\theta - \beta\cos\theta + j\alpha\cos\theta}{\sin^2\theta + \beta\cos\theta - j\alpha\cos\theta}\right)$$

$$r_v(\theta) = r_h(\theta)\left(\frac{\sin\theta\tan\theta - \beta + j\alpha}{\sin\theta\tan\theta + \beta - j\alpha}\right)$$

For the quantities between the bracketed terms of Equations 14 to have equal values:

$$\sin\theta\tan\theta = \cos\theta$$

$$\tan^2\theta = 1 \qquad \text{Equations 15}$$

Solving Equations 15 for θ results in:

$$\theta = \pi/4$$

Therefore, at θ=π/4, the following relationship can be ascertained:

$$\frac{r_v(\pi/4)}{r_h(\pi/4)} = r_h(\pi/4) \qquad \text{Equation 16}$$

Equation 16 thus indicates that at an incidence angle θ of 45° (π/4 radian), the ratio of vertical over the horizontal Fresnel reflection coefficients is equal to the horizontal Fresnel reflection coefficient.

The reflectivities $R_h(\theta)$, and $R_v(\theta)$ can be related to the reflection coefficients as follows:

$$R_h(\theta) = r_h(\theta)r_h^*(\theta)$$

$$R_v(\theta) = r_v(\theta)r_v^*(\theta) \qquad \text{Equations 17}$$

Where:
"*" terms are complex conjugates.

In the case of a rough interface of the material 202, the equality between the reflectivity ratio and horizontal reflectivity shifts away from 45°. Values of reflectivities for a more rough interface of the material 202 are based on a small perturbation technique where the coherent horizontal $R_{ch}(\theta)$ and vertical $R_{cv}(\theta)$ reflectivities could be written as:

$$R_{ch}(\theta) \approx R_h(\theta)\exp(-4k^2\sigma^2\cos^2\theta)$$

$$R_{cv}(\theta) \approx R_v(\theta)\exp(-4k^2\sigma^2\cos^2\theta) \qquad \text{Equation 18}$$

Where:
σ is a variance of the interface roughness;
k=2π/λ; and
λ is the wavelength.

From Equations 18, as the surface variance vanishes (i.e., σ=0), the coherent vertical and horizontal reflectivities $R_{cv}(\theta)$, $R_{ch}(\theta)$ reduce to the vertical and horizontal reflectivities $R_v(\theta)$, $R_h(\theta)$, respectively. The equality at 45° between the reflectivity ratio and the horizontal reflectivity in case of a smooth planar interface, and the deviation of the equality from the 45° angle in case of rough interface can be used by the processing unit 18 for measuring surface roughness of the material 206.

Figure 6:
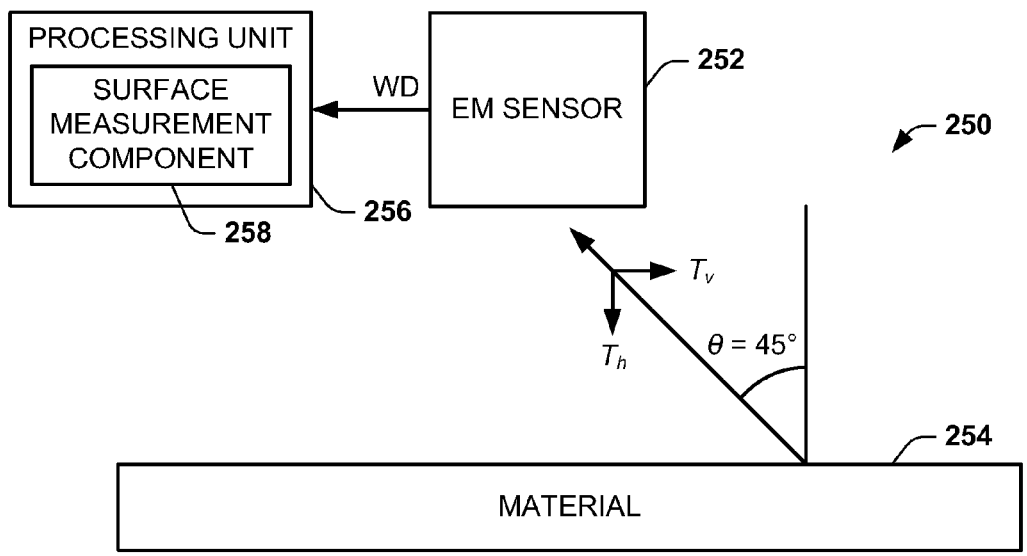
FIG. 6 illustrates yet another example diagram of collecting radiation in accordance with an aspect of the invention.

FIG. 6 illustrates another example of a material detection system 250 in accordance with an aspect of the invention. The diagram 250 includes an EM sensor 252 that can correspond to the EM sensor 12 in the example of FIG. 1, such as can be implemented for measuring surface roughness of a material 16 in the example of FIG. 1 or 206 in the example of FIG. 5. Therefore, reference is to be made to the examples of FIGS. 1 and 5 in the following description of the example of FIG. 6.

As an example, the EM sensor 252 can be configured as a dual-polarized radiometer that operates at MMW frequencies. The EM sensor 252 can thus acquire thermal radiation emitted from a surface of a material 254 to be tested in the form of both a vertical brightness temperature $T_v(\theta)$ and a horizontal brightness temperature $T_h(\theta)$. The vertical brightness temperature $T_v(\theta)$ and the horizontal brightness temperature $T_h(\theta)$ can be acquired at an incident angle of approximately 45°. In calculating the surface roughness of the surface of the material 254, the depth of the surface of the material 254 can be taken to be greater than an electric skin depth at the operating frequency of the EM sensor 252 and can have a uniform physical temperature T, such as can be acquired from an IR radiometer similar to as described above. Furthermore, a sky temperature can be corrected for in the calculation of the surface roughness. The vertical and horizontal brightness temperatures $T_v(\theta)$, $T_h(\theta)$ acquired by the EM sensor 252 could be written as:

$$T_v = e_v(\theta)T$$

$$T_h = e_h(\theta)T \qquad \text{Equations 19}$$

Where:
$e_v(\theta)$ is a vertical emissivity; and
$e_h(\theta)$ is a horizontal emissivity.

The vertical and horizontal reflectivities $R_v(\theta)$, $R_h(\theta)$ are related to the respective vertical and horizontal emissivities $e_v(\theta)$, $e_h(\theta)$ as follows:

$$e_v(\theta) = 1 - R_{cv}(\theta)$$

$$e_h(\theta) = 1 - R_{ch}(\theta) \qquad \text{Equations 20}$$

The EM sensor 252 provides the vertical and horizontal brightness temperatures $T_v(\theta)$, $T_h(\theta)$, as well as the physical temperature T from an IR radiometer such as incorporated into the EM sensor 252, to a processing unit 256. For example, the IR radiometer can operate substantially similar to the IR radiometer described in Applicant's co-pending application Ser. No. 13/432,558 entitled: "Systems and Methods for Detecting and/or Identifying Materials", filed simultaneously herewith. As an example, the processing unit 256 could correspond to the processing unit 18 in the example of FIG. 1. In the example of FIG. 6, the processing unit 256 includes a surface measurement component 258 configured to measure the surface roughness of the material 254, as described in greater detail below.

The surface measurement component 258 can divide the vertical and horizontal brightness temperatures $T_v(\theta)$, $T_h(\theta)$ over the physical temperature T to extract the vertical and horizontal emissivities $e_v(\theta)$, $e_h(\theta)$ by implementing Equations 19. Upon obtaining the vertical and horizontal emissivities $e_v(\theta)$, $e_h(\theta)$, the surface measurement component 258 can incorporate them into Equations 20 to extract the vertical and horizontal reflectivities $R_v(\theta)$, $R_h(\theta)$. The surface measurement component 258 can determine the ratio of vertical reflectivity $R_v(\theta)$ over the horizontal reflectivity $R_h(\theta)$ and the horizontal reflectivity $R_h(\theta)$. If the ratio is approximately equal, the surface measurement component 258 determines that the surface of the material 254 is smooth, such that the processing unit 256 proceeds to extract the refractive index for accurately identification of the material 254. If the ratio is not equal, the surface measurement component 258 determines that the surface of the material 254 is rough and estimates the surface variance σ as follows:

$$\sigma = \frac{\lambda}{2\pi}\sqrt{0.5\ln[R_{cv}(\pi/4)] - \ln[R_{ch}(\pi/4)]} \qquad \text{Equation 21}$$

Upon estimating the surface variance σ, the processing unit 256 can implement the surface variance σ to correct reflectivity data. The processing unit 256 can then exploit the corrected reflectivity data in identifying the material 254. As an example, Equation 21 can be obtained by dividing Equations 18 to obtain the following:

$$\frac{R_{cv}(\pi/4)}{R_{ch}(\pi/4)} = \frac{R_v(\pi/4)}{R_h(\pi/4)} \qquad \text{Equation 22}$$

From the relationship identified in Equation 16, the horizontal coherent reflectivity of Equation 18 can be expressed as:

$$R_{ch}(\pi/4) \approx R_h(\pi/4)\exp(-2k^2\sigma^2)$$
$$\frac{R_{cv}(\pi/4)}{R_{ch}(\pi/4)} = R_{ch}(\pi/4)\exp(2k^2\sigma^2) \qquad \text{Equations 23}$$

The logarithm of Equations 23 can then be expressed as:

$$k^2\sigma^2 = 0.5\, \ln(R_{cv}(\pi/4)) - \ln(R_{ch}(\pi/4)) \qquad \text{Equation 24}$$

Therefore, applying a square root to Equation 24 and setting $k=2\pi/\lambda$ results in Equation 21. As a result, the determination of the surface roughness of the material 254 by the surface measurement component 258 can correct the reflectivity data calculated by the processing unit 256 in detecting and/or identifying the material 254 based on an accurate calculation of the refractive index of the material 254. As a result, the processing unit 252 can accurately identify the material 254.

It is to be understood that the material 254 in the example of FIG. 6 is not limited to an explosive material, but could be any of a variety of materials for which an accurate refractive index may be desired to be calculated. In addition, while the example of FIG. 6 describes adjusting reflectivity for accurate determination of the refractive index of the material 254, it is to be understood that other calculations could be adjusted based on the determination of the surface roughness of the material 254. For example, the processing unit 256 could be configured to detect and/or identify the material 254 based on dielectric constant, such as described in Applicant's co-pending application Ser. No. 13/432,558 entitled: "Systems and Methods for Detecting and/or Identifying Materials", filed simultaneously herewith. As a result, the adjusted reflectivity of the material 254 as determined based on the surface roughness measured by the surface measurement component 258 could be implemented to adjust the reflectivity of the material 254 for detection and/or identification of the material 254 based on the dielectric constant of the material 254.

Figure 7:
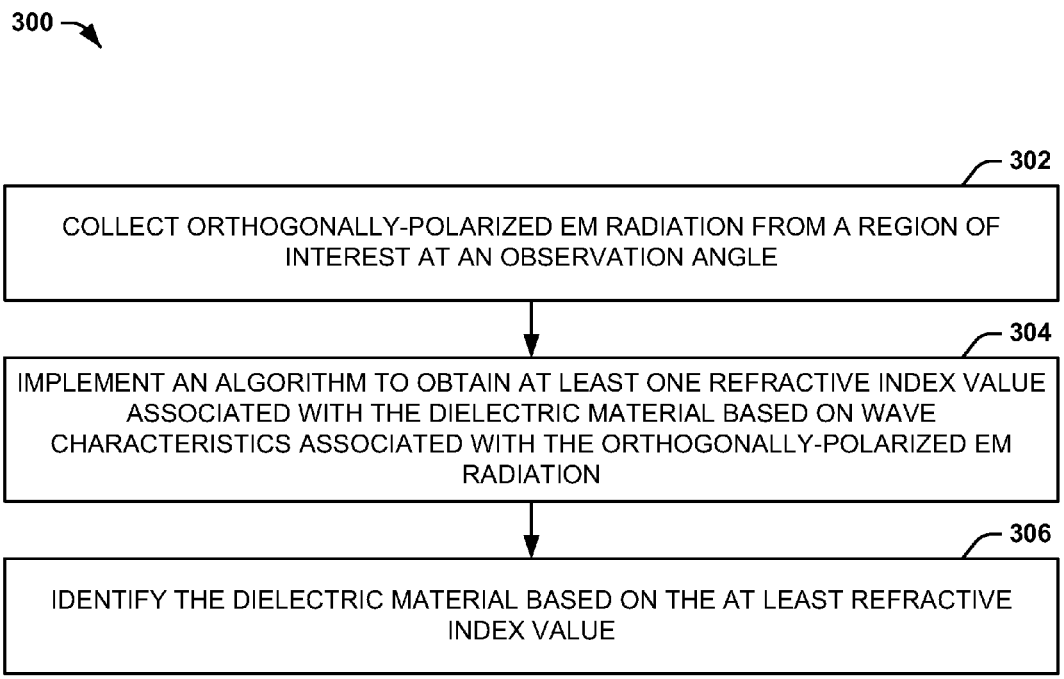
FIG. 7 illustrates an example of a method for detecting and identifying a material in a region of interest in accordance with an aspect of the invention.
Figure 8:
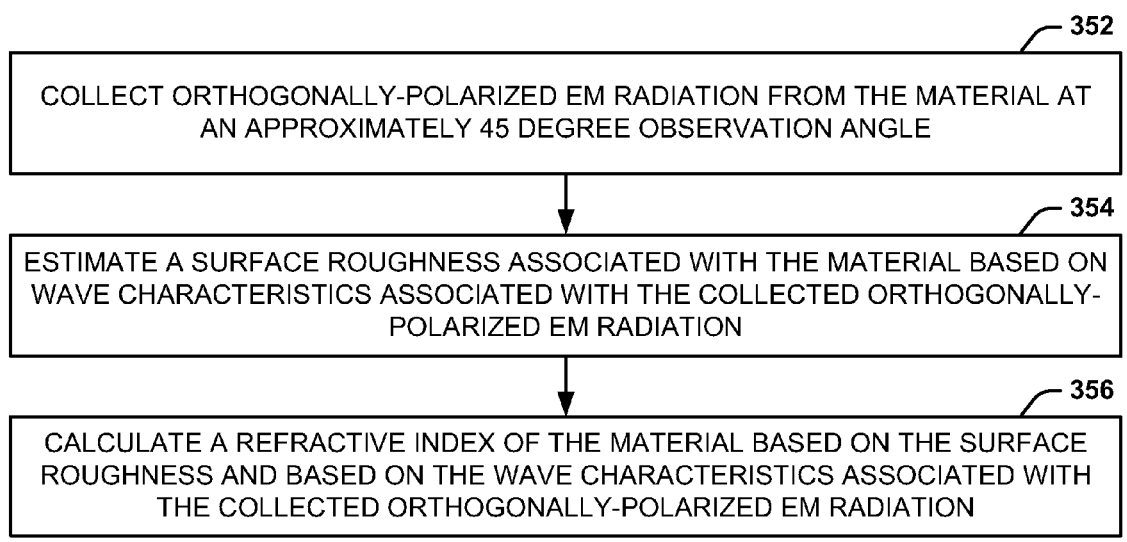
FIG. 8 illustrates another example of a method for determining a refractive index of a material in accordance with an aspect of the invention.

In view of the foregoing structural and functional features described above, methodologies in accordance with various aspects of the present invention will be better appreciated with reference to FIGS. 7 and 8. While, for purposes of simplicity of explanation, the methodologies of FIGS. 7 and 8 are shown and described as executing serially, it is to be understood and appreciated that the present inventions are not limited by the illustrated order, as some aspects could, in accordance with the present inventions, occur in different orders and/or concurrently with other aspects from that shown and described herein. Moreover, not all illustrated features may be required to implement a given methodology in accordance with aspects of the present inventions.

FIG. 7 illustrates another example of a method 300 for detecting and identifying a material in a region of interest in accordance with an aspect of the invention. At 302, orthogonally-polarized EM radiation is collected from a region of interest at an observation angle. The orthogonally-polarized radiation can be collected via an orthogonally-polarized radiometer, which can be a passive radiometer or an active scatterometer configured as a backscattering or bi-static scatterometer/radar. At 304, an algorithm is implemented to obtain at least one refractive index value associated with the dielectric material in the region of interest based on wave characteristics associated with the collected orthogonally-polarized radiation. The at least one refractive index value can be obtained based on calculating orthogonally-polarized reflectivity data associated with the dielectric material, a scene physical temperature of the region of interest, and an observation angle associated with the EM sensor system. At 306, the dielectric material can be identified based on the at least one refractive index value. The at least one refractive index value can be compared with refractive index data in a database to identify the dielectric material. The database can include a list of refractive indices of known explosives to determine the identity of the material as a specific type of explosive material.

FIG. 8 illustrates an example of a method 350 for determining a refractive index of a material in accordance with an aspect of the invention. At 352, orthogonally-polarized radiation is collected from the material at an approximately 45 degree observation angle. The radiation can be collected via a radiometer. The collected radiation can be MMW radiation. At 354, a surface roughness associated with the material is estimated based on wave characteristics associated with the collected orthogonally-polarized radiation. The surface roughness can be estimated based on acquiring horizontal and vertical reflectivities associated with the material, and based on a ratio of ratio of the vertical reflectivity over the horizontal reflectivity with the horizontal reflectivity. At 356, a refractive index of the material is calculated based on the surface roughness of the material and based on wave characteristics associated with the collected orthogonally-polarized radiation. The surface roughness estimate can be used to correct reflectivity data, which is then used to calculate the refractive index.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A material detection system comprising:
   an electromagnetic (EM) sensor system configured to collect radiation from a region of interest; and
   a processing unit configured to measure reflectivity data associated with a material of interest in the region of interest based on the collected radiation and to calculate a refractive index of the material of interest based on the measured reflectivity data, the processing unit being further configured to identify the material of interest based on the refractive index of the material of interest.

2. The system of claim 1, wherein the EM sensor system is configured as a dual-polarized radiometer, such that the reflectivity data is measured as orthogonally-polarized reflectivity data.

3. The system of claim 1, wherein the EM sensor system is configured as an active radiometer comprising a transmitter and a receiver.

4. The system of claim 1, wherein the processing unit is configured to measure the reflectivity data based on orthogonally-polarized brightness temperatures at an observation angle and a scene physical temperature associated with the region of interest.

5. The system of claim 1, wherein the processing unit further comprises a database configured to store refractive index data associated with a plurality of materials, wherein the processing unit is further configured to identify the material of interest based on comparing the refractive index of the material of interest with the refractive index data stored in the database.

6. The system of claim 1, wherein the processing unit is configured to calculate real and imaginary components of a relative dielectric constant of the material of interest based on the reflectivity data associated with the material of interest and an observation angle associated with the EM sensor system, the processing unit being further configured to calculate the refractive index of the material of interest as complex refractive index components based on the real and imaginary components of the relative dielectric constant of the material of interest.

7. The system of claim 1, wherein the EM sensor system is configured to collect the radiation at an observation angle of approximately 45 degrees, and wherein the processing unit is further configured to calculate a surface roughness of the material of interest based on the wave characteristics of the collected radiation and to adjust the calculated refractive index based on the calculated surface roughness.

8. A method for detecting and identifying a material in a region of interest, the method comprising:
    collecting orthogonally-polarized electromagnetic (EM) radiation from a region of interest at an observation angle;
    implementing an algorithm to obtain at least one refractive index value associated with a dielectric material in the region of interest based on wave characteristics associated with the collected orthogonally-polarized EM radiation; and
    identifying the dielectric material based on the at least one refractive index value.

9. The method of claim 8, further comprising:
    collecting infrared (IR) radiation of the region of interest that includes the dielectric material; and
    determining the physical temperature of the region of interest based on the collected IR radiation, wherein implementing the algorithm comprises obtaining at least one refractive index value based on the collected orthogonally-polarized EM radiation of the region of interest and the physical temperature of the region of interest.

10. The method of claim 8, wherein collecting the orthogonally-polarized EM radiation comprises collecting the orthogonally-polarized EM radiation from the region of interest via one of a passive radiometer and a scatterometer/radar at the observation angle.

11. The method of claim 8, further comprising calculating orthogonally-polarized reflectivity data based on the orthogonally-polarized EM radiation, wherein implementing the algorithm comprises implementing the algorithm to obtain the at least one refractive index value associated with the dielectric material in the region of interest based on the orthogonally-polarized reflectivity data.

12. The method of claim 11, wherein identifying the dielectric material comprises comparing the at least one refractive index value of the dielectric material with refractive index data associated with a plurality of materials stored in a database.

13. The method of claim 8, wherein collecting the orthogonally-polarized EM radiation comprises collecting orthogonally-polarized EM radiation from a region of interest at an observation angle of approximately 45 degrees, the method further comprising:
    calculating a surface roughness of the material of interest based on the wave characteristics of the collected EM radiation; and
    adjusting the at least one refractive index of the material of interest based on the calculated surface roughness.

14. A non-transitory computer readable medium configured to implement a method for determining a refractive index of a material, the method comprising:
    collecting orthogonally-polarized EM radiation from the material at an approximately 45 degree observation angle;
    estimating a surface roughness associated with the material based on wave characteristics associated with the collected orthogonally-polarized EM radiation; and
    calculating a refractive index of the material based on the surface roughness of the material and based on the wave characteristics associated with the collected orthogonally-polarized EM radiation.

15. The method of claim 14, further comprising:
    collecting infrared (IR) radiation of a region of interest that includes a dielectric material; and
    determining the physical temperature of the region of interest based on the collected IR radiation of the region of interest, wherein calculating the refractive index of the material comprises calculating the refractive index of the material based on the surface roughness of the material, the physical temperature of the region of interest, and the wave characteristics associated with the collected orthogonally-polarized EM radiation.

16. The method of claim 14, wherein acquiring the reflectivity data comprises acquiring a horizontal reflectivity data and a vertical reflectivity data, and wherein estimating a surface roughness comprises comparing a ratio of the vertical reflectivity over the horizontal reflectivity with the horizontal reflectivity.

17. The method of claim 14, wherein collecting the orthogonally-polarized EM radiation comprises collecting orthogonally-polarized millimeter wave (MMW) radiation.

18. The method of claim 14, further comprising acquiring reflectivity data associated with the material based on the collected orthogonally-polarized EM radiation, wherein estimating the surface-roughness comprises estimating the surface-roughness based on the reflectivity data.

19. The method of claim 18, wherein acquiring the reflectivity data comprises calculating vertical and horizontal reflectivities associated with the material, and wherein estimating the surface-roughness further comprises calculating a surface variance based on a comparison of a ratio of the vertical reflectivity over the horizontal reflectivity with the horizontal reflectivity.

20. The method of claim 14, wherein calculating the refractive index comprises:
    calculating a surface variance based on horizontal and vertical reflectivities associated with the material;
    correcting reflectivity data associated with the material based on the calculated surface variance; and
    calculating the refractive index of the material based on the corrected reflectivity data.

* * * * *